United States Patent [19]
Zakaria et al.

[11] Patent Number: 5,320,804
[45] Date of Patent: * Jun. 14, 1994

[54] PROCESS AND APPARATUS FOR CONTROLLED MICROWAVE HEATING UNDER PRESSURE

[75] Inventors: Zairani Zakaria, Charlotte, N.C.; Edwin D. Neas, St. Paul, Minn.

[73] Assignee: CEM Corporation, Matthews, N.C.

[*] Notice: The portion of the term of this patent subsequent to Jan. 28, 2009 has been disclaimed.

[21] Appl. No.: 868,309

[22] Filed: Apr. 14, 1992

Related U.S. Application Data

[63] Continuation-in-part of Ser. No. 352,003, May 15, 1989, Pat. No. 5,108,701.

[51] Int. Cl.$^5$ .............................................. A61L 2/12
[52] U.S. Cl. ........................................ 422/21; 422/25; 422/108; 422/112; 422/116; 422/307; 219/759; 219/686
[58] Field of Search ............... 219/10.55 B, 10.55 F, 219/10.55 R, 10.55 M; 422/3, 21, 25, 41, 105, 108, 109, 112, 116, 119, 295, 299, 307

[56] References Cited

U.S. PATENT DOCUMENTS

| | | | |
|---|---|---|---|
| 3,404,946 | 10/1968 | Reis | 422/108 |
| 3,571,563 | 3/1971 | Shulz | 422/112 X |
| 3,706,631 | 12/1972 | Falk | 422/21 |
| 4,093,841 | 6/1978 | Dills | 219/10.55 B X |
| 4,258,971 | 2/1981 | Youssef | 435/253.6 |
| 4,297,557 | 10/1981 | Tyler et al. | 219/10.55 B X |
| 4,393,088 | 7/1983 | Matsusaka | 426/234 |
| 4,613,738 | 9/1986 | Saville | 219/10.55 R X |
| 4,671,935 | 6/1987 | Rohrer et al. | 422/21 |
| 4,691,087 | 9/1987 | Lee | 219/10.55 B |
| 4,835,354 | 5/1989 | Collins et al. | 219/10.55 B |
| 4,877,624 | 10/1989 | Floyd | 219/10.55 R |
| 4,904,450 | 2/1990 | Floyd | 422/113 |
| 5,122,633 | 6/1992 | Moshammer et al. | 219/10.55 M X |
| 5,124,125 | 6/1992 | Brent | 422/21 |

FOREIGN PATENT DOCUMENTS

| | | |
|---|---|---|
| 0155788 | 7/1982 | Fed. Rep. of Germany. |
| 3612606 | 2/1988 | Fed. Rep. of Germany. |
| 0202275 | 6/1981 | Japan. |
| 0069566 | 10/1981 | Japan. |
| 8006912 | 10/1980 | Sweden. |
| 1222208 | 2/1971 | United Kingdom. |

OTHER PUBLICATIONS

Latimer et al., J. Clin. Microbiol., vol. 6, pp. 340–342 (1977).
Bailey et al., Biochemical Engineering Fundamentals, 2nd Ed., pp. 586–591 (1986).

*Primary Examiner*—James C. Housel
*Assistant Examiner*—Jeffrey R. Snay
*Attorney, Agent, or Firm*—Raymond F. Kramer

[57] ABSTRACT

A process for rapidly sterilizing biological media, such as broths and gels used as incubation or growth media to test the presence of microorganisms, such as bacteria, includes applying microwave radiation to such an aqueous biological medium contained in a microwave transmissive pressure retaining container, such as a capped cylinder made of polytetrafluoroethylene, which cap is preferably equipped with ports, by directing the microwave radiation through the container and onto the medium in such amount that the pressure in the container and the temperature of the medium are raised above ambient pressure and temperature, and maintaining such raised pressure and temperature for a time sufficient to sterilize the medium. In a preferred operation the microwave heating at elevated pressure and temperature takes place for about five minutes, the pressure during that time is 30 to 50 psig, the microwave heating of the medium takes place in a radiation confining chamber of a microwave apparatus, a plurality of containers for the biological medium is present in such chamber, the containers are kept in motion by an oscillating turntable, and the pressure in at least one container is monitored and the application of microwave radiation is controlled in response to that pressure. In a broader process aspect the contained material is heated but not necessarily sterilized. Also within the invention is the apparatus utilized in the described process.

17 Claims, 4 Drawing Sheets

PROCESS AND APPARATUS FOR CONTROLLED MICROWAVE HEATING UNDER PRESSURE

This application is a continuation-in-part of our application Ser. No. 07/352,003, filed May 15, 1989, now U.S. Pat. No. 5,108,701, issued Apr. 2, 1992.

This invention relates to a process and an apparatus for controllable microwave heating of materials under pressure. More particularly, it relates to an improved, quick sterilization process which utilizes microwave radiation and pressure, speedily and effectively to sterilize biological media, such as incubating broths and gels, e.g., soy broth and agar gels, but it is also applicable to sterilizing other materials, including both solids and liquids, and it relates to suitable apparatus for effecting such a process.

The use of microwave radiation for cooking is well known and is familiar to almost everybody. Microwave radiation has been employed industrially for heating a wide variety of products during manufacturing, which products include such diverse materials as toothpastes, polymers and paints (to promote curing) and gums (to promote dissolving). Microwaving has been employed to dry various polar solid and suspensions, such as milk and cheese, fruits and sewage. It has also been employed to preserve and sometimes sterilize many other materials, such as packaged foods, fish, ampoules, proteinaceous products, bandages, pharmaceuticals, and water. In most instances such microwave heating, drying, preservation and sterilization have been conducted under atmospheric pressure but sometimes the materials heated have been in enclosed containers so that the heating thereof was under pressure, which allowed the temperature of the treated medium to be raised.

Despite the widespread use of microwave radiation, so far as applicants know, prior to their invention it was not employed to sterilize biological media nor was it employed with an oscillating turntable, a pressurized container of material to be heated, control means to actuate a source of microwave radiation in response to a pressure in the container that is lower than desired, and a means for communicating the container pressure with the pressure responsive controller. Biological media are conventionally sterilized by means of autoclaves, before being used to grow colonies of microorganisms (or being employed to ascertain that such organisms are not present in test samples in a viable state). Autoclaves that are employed for such purpose are of substantial masses and although they may be heated to sterilizing temperature rather quickly by electric resistance heating elements they take comparatively long to cool down sufficiently so that they can be opened and so that the containers of biological media can be safely removed. Thus, sterilization in an autoclave might take thirty minutes or more for the heating-sterilization-cooling process whereas, depending on the number of containers of media to be sterilized and the microwave power applied, sterilization by the present invented method may often be effected in about ten minutes or less. The substantial difference between the times required for the total process is significant because it allows quicker responses to requirements for media for culturing specimens from industrial facilities or production lines without the need to keep an inventory of sterile media, which often have to be of different types. It also increases the efficiency of the microbiologist or technician overseeing or performing the sterilizations and increases the number of sterilizations that can be effected in a normal working day. Additionally, the invented process is adaptable to producing relatively large or small quantities of one or more of different sterilized media and the operation of the equipment employed is easy, safe and effective.

In accordance with the present invention a process for heating aqueous material in a container under pressure to a desired elevated temperature level or range and maintaining it at that level or range comprises applying microwave radiation to such material in a closed pressure retaining container by directing microwave radiation through the container and onto the material in the container while the container is moving in oscillating rotational motion so that the pressure and temperature in the container are elevated, with the container interior being connected by connecting means to a controller, which is activated by the pressure in the container, which controller controls the microwave radiation onto the container and its contents so that the pressure in the container is maintained at such a level or in such a range as to cause the temperature therein to be at the desired level or in the desired range.

In a more limited aspect of the invention a process for rapidly sterilizing biological media comprises applying radiation to an aqueous biological medium, contained in a microwave transmissive pressure retaining container, by directing the microwave radiation through the container and onto the medium in such amount that the pressure in the container and the temperature of the medium are raised above ambient pressure and temperature, and maintaining such raised pressure and temperature for a short time, less than ten minutes, sufficient to sterilize the medium. Preferably the biological medium is a broth or gel forming medium which is suitable for growing bacterial colonies, the sterilizing time is in the range of 3 to 10 minutes, more preferably about 5 minutes, 1, 2 or 5 to 20 containers of medium are sterilized at the same time, the pressure during sterilization is in the range of 15 or 30 to 50 or 100 psig, more preferably 30 or 35 or 40 psig, and the temperature of the medium during sterilization is in the range of 120° to 170° C., more preferably about 130° C. In other preferable embodiments of the invention the essential biological medium components, in powder or tablet form, and water, are added to the container prior to application of the microwave radiation so that the components are dissolved in the water during the sterilizing heating thereof by the microwave radiation. After sterilization the medium is cooled so that the pressure in the container is lowered, the container is opened, and the sterilized medium is poured into an incubating container or into a plurality of such containers. During the sterilization it is preferred for a digitally controlled microwave apparatus to be employed to controllably heat the containers of media and to maintain them at a sterilizing pressure (and temperature), with the containers being kept in motion, preferably by a turntable in the microwave apparatus chamber, so as to provide even heating of the media, and it is preferred that a monitor be provided, with a digital readout, so that the pressures in the container(s) may be followed by the operator of the apparatus. The monitor is preferably integral with the pressure controller, which is usually stationary and which is connected to the moving container by the connecting means, which is usually a flexible tube.

In its apparatus aspect the present invention is of an apparatus for controllably heating material in a pressure retaining container, which includes a microwave chamber, a source of microwave radiation, a turntable in the microwave chamber that can move in oscillating rotational motion, a pressure responsive controller which controls the source of microwave radiation in response to pressure communicated to it, and means for connecting the controller with the pressure retaining container for the material to be heated, when such container is on the turntable, which is in oscillating rotational motion, whereby such material is controllably heated. Preferably the apparatus includes a horizontal turntable which is capable of supporting 1 to 20 containers of material to be heated and sterilized, and is movable at 3 to 20 oscillations per minute, with the oscillations being in the 180° to 360° or 180° to 540° ranges, e.g., 360°.

In a computer search of the World Patent Index (DIALOG Files 350 and 351) several references were found to sterilizing materials under pressure. U.S. Pat. No. 3,706,631 describes the employment of microwave radiation to heat human blood serum to a temperature in the range of 124°-135° C. U.S. Pat. No. 3,737,608 describes the sterilization of incompletely filled medicine ampoules or sealed beverage containers by irradiating them with microwave energy while the containers are in motion. U.S. Pat. No. 3,692,616 described the sterilization of pre-packaged nutrients, such as cheeses or microcultures, in fluid filled pressure containers, using microwaves, while circulating a coolant, which displaces the fluid medium. British specification 1,222,208 teaches the production of sterile packaged material by force feeding the material into a vessel so that it is pressurized in such vessel, and applying microwave energy to the exterior of the vessel. U.S. Pat. No. 3,494,722 describes sterilization of articles in a container under pressure by means of microwave radiation. The articles are moved through a pressurized chamber and through a high intensity microwave field therein until they are sterile. West German specification 3,612,606 describes sterilization of materials, such as pharmaceuticals in ampoules, by microwave radiation, when the ampoules are maintained under an external pressure, to prevent bursting at the sterilizing temperature, which may be about 121° C. In U.S. Pat. No. 4,490,597 food is cooked in a container by radiating it with microwaves. The container includes a pressure regulating mechanism. Similar subject matter is described in U.S. Pat. Nos. 4,400,401, 4,406,860, 4,406,861, and 4,409,454. Sterilization of food products under pressure is also described in Japanese patents 57202275 and 58069566. East German patent 155,788 describes the production of dried microbial cell material by heating such material at elevated pressure by means of microwaves. Swedish patent 8006912 relates to sterilization of medical and odontological instruments in a sealed chamber in which they are subjected to high pressure steam produced by microwave radiation. U.S. Pat. No. 4,400,357 describes microwave sterilization of medical and dental tools which are in a sealed bottle that also contains a liquid, which is vaporizable by microwave radiation thereof, with the tools being separated from the liquid by a perforated disc. In U.S. Pat. No. 4,393,088 microwaves are employed to sterilize food in a sealed container which is transmissive of microwaves.

The present invention will be readily understood by reference to the description of a preferred embodiment thereof in this specification, including the drawing, in which.

Figure 1:
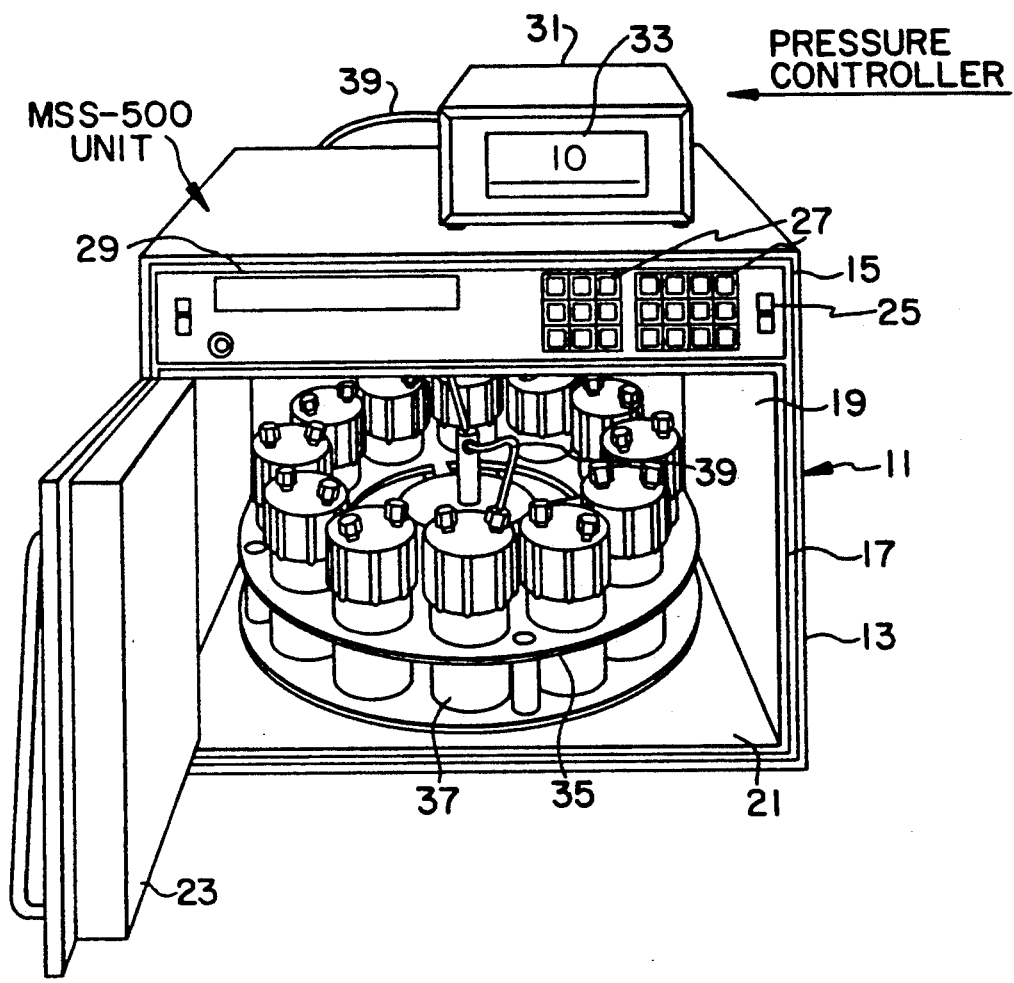
FIG. 1 is a front perspective view of the microwave sterilization system of the invention, showing twelve containers of culture media mounted on an oscillating turntable in a digitally controlled microwave apparatus equipped with a pressure controller to control the pressure in the containers by regulating the amount of microwave radiation directed onto them.

In FIG. 1 there is illustrated CEM's Microwave Sterilization System apparatus 11, which is also designated as CEM MSS 500. The apparatus is a modification of an earlier microwave heating system manufactured by CEM Corporation, which identifies it as MDS-81. Such earlier apparatus is described in a brochure entitled CEM Corporation Microwave Drying/Digestion System, MDS-81, Laboratory Microwave System, which was published in 1981. Such an apparatus is also described in U.S. Pat. No. 3,909,598, assigned to CEM Corporation, and in U.S. patent application Ser. No. 07/189,727, issued as U.S. Pat. No. 4,835,354, and Ser. No. 07/298,554, abandoned, all of which are hereby incorporated by reference.

Apparatus 11 includes an external cabinet casing 13, which encloses, primarily in an upper portion 15 thereof, controls and displays, and a source of microwave radiation, and in a lower portion, a microwave radiation confining chamber 17, which includes wall and floor members 19 and 21, and door 23. Upper portion 15 includes on-off button 25, digital controls 27 and alpha-numeric display 29. Atop the integral microwave apparatus casing 13 is a digital electronic pressure controller, which, in response to a pressure signal transmitted to it, turns a magnetron, not illustrated, on or off, or alternatively or also, regulates the amount of power to the magnetron so as to maintain a desired set pressure in a microwave transmissive and pressure retaining container 37 or a plurality of such containers in the apparatus. As illustrated, pressure controller 31 includes a display portion 33 for indicating the pressure in the sterilizing container(s) in the apparatus during operation thereof.

Inside the chamber 17 is a turntable 35 suitable for holding a plurality of the sterilizing containers, which containers will be described in more detail subsequently. In the modified apparatus of the present invention flexible tubing 39 communicates an upper portion of container 37 with pressure controller and monitor 31. As illustrated, the pressure controller also serves as a monitor to give a visual report of the pressure in containers 37 but in some instances separate controllers and monitors may be utilized.

In FIG. 1 various conventional parts of a microwave apparatus have not been specifically shown because illustrating them would make the drawing unnecessarily complicated. Such parts include the magnetron, wave guide, magnetron cooling fan, electronic circuitry (including microprocessor), circulating fan (for circulating air through the microwave apparatus chamber), and inlet and outlet ports. However, one of skill in the art will know where such are located, and reference may be had to the bulletin, patent(s) and application(s) previously mentioned for further information.

Figure 2:
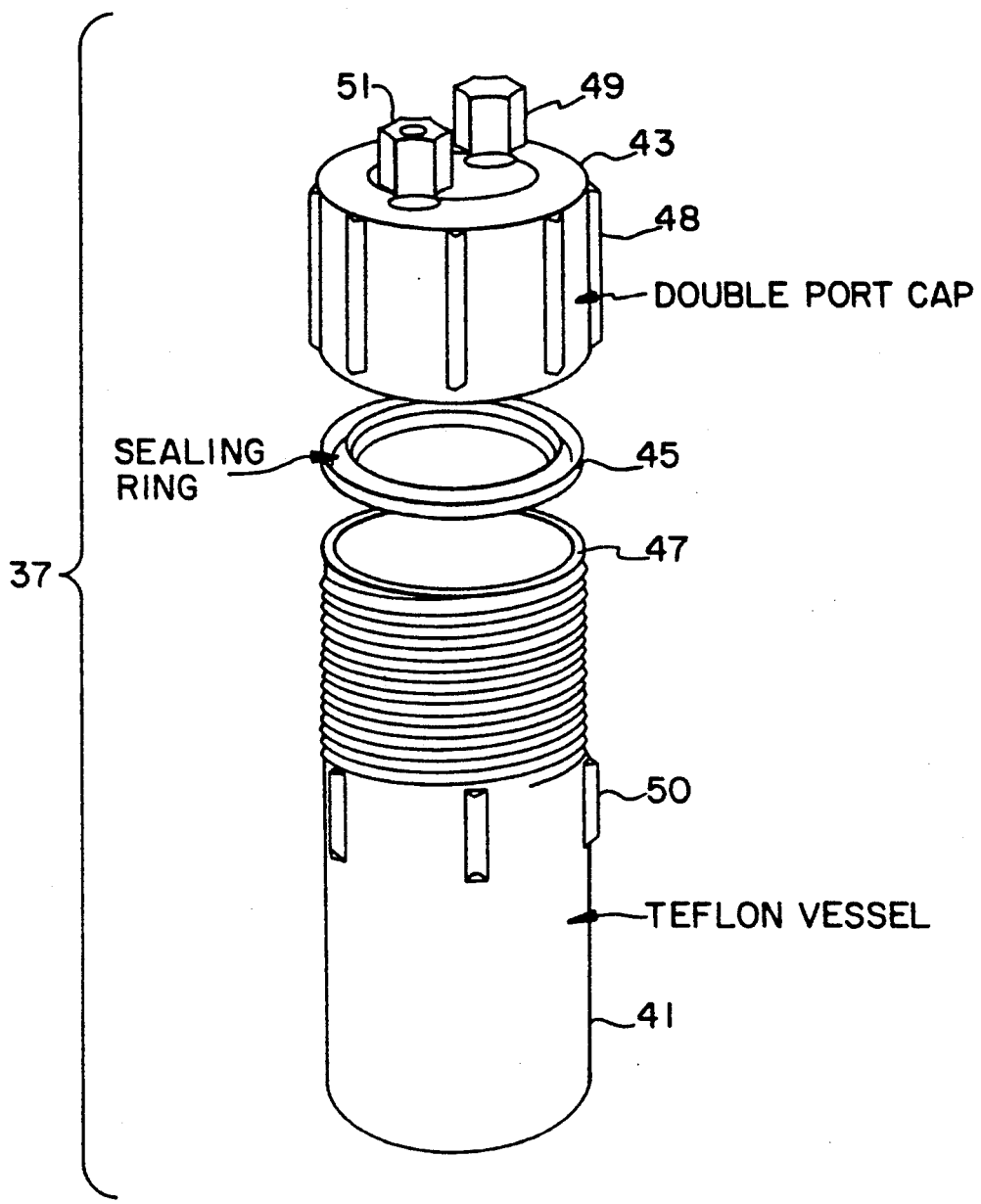
FIG. 2 is a disassembled view of a container in which culture medium is sterilized in the microwave sterilization system of FIG. 1.

In FIG. 2 container 37 includes threaded cylindrical lower portion 41, cap 43 and gasket or sealing ring 45. Cap 43 is internally threaded so that it screws onto cylindrical container 41, with a tight seal being made by pressing of an internal upper portion of the cap against the sealing ring 45, which also presses against the upper edge 47 of the cylinder, making a pressure-tight seal. Ridges 48 and 50 are provided on the cap and on the cylinder, respectively, for hand grips, and additionally perform strengthening functions. Container cap 43 is equipped with a pair of molded-in nipples, to serve as ports, so that the internal pressure in the container during operation may be transmitted to other such vessel(s) and/or to a pressure controller and/or monitor. As illustrated, one of such ports is blanked off with cap 49 and the other is adaptable, by means of fitting 51, to connect a pressure holding tubing to such other container, controller and/or monitor. Further details of the microwave transmitting and pressure retaining container construction will be given in the immediately following description of the apparatus of FIG. 3.

Figure 3:
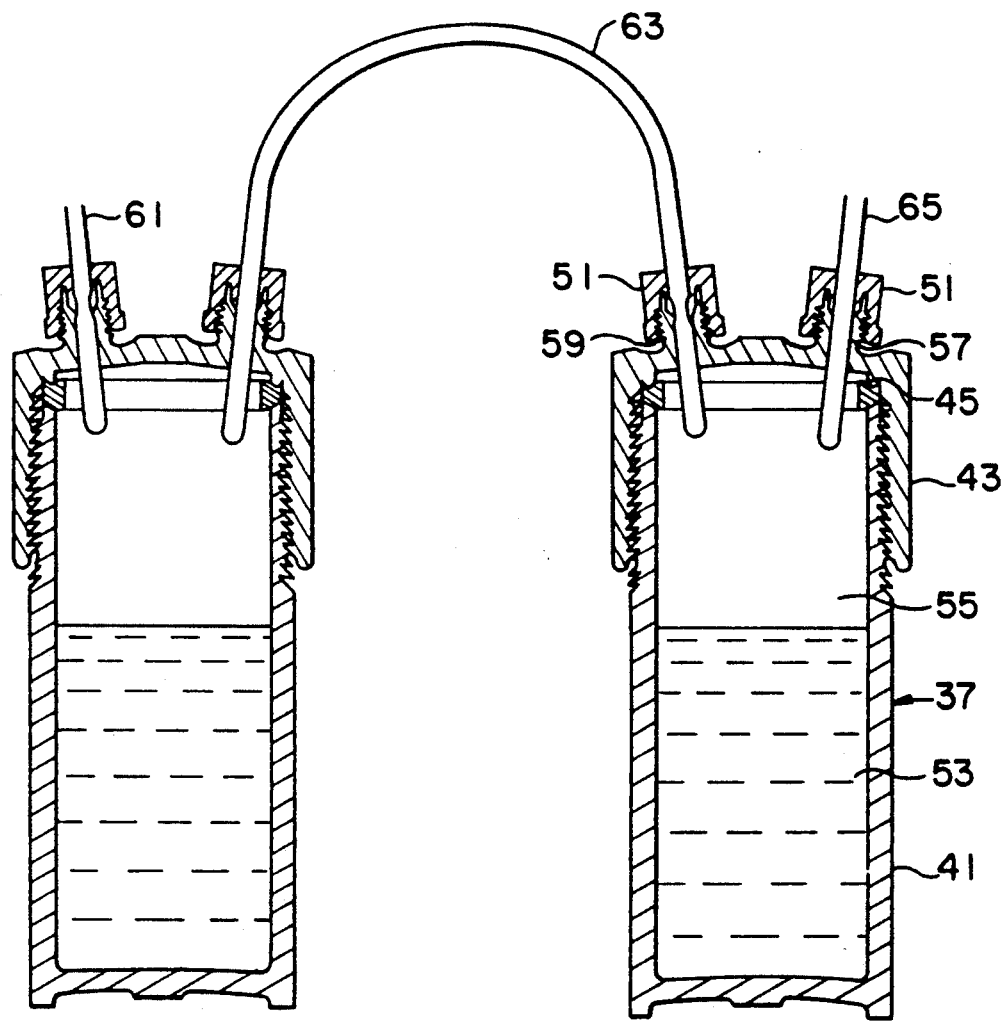
FIG. 3 is a vertical sectional view of a pair of containers like that illustrated in FIG. 2, with a pressure equalizing tubing connection between them and with tubing connections suitable for communication with a pressure controller and a pressure monitor.

FIG. 3 illustrates a pair of containers of the type shown in FIG. 2, connected together so as to equalize or average the pressures in them. The containers are identical so numerals will be applied to only one of them. The containers illustrated are of about 125 ml. capacities and contain little over halves of their volumes of a biological culture medium, which may be a bacteriological medium for growing bacterial colonies. Such a medium, when sterile, is useful in determining the presence or absence of bacteria in a specimen or for measuring the content of bacterial cells in a specimen. Above the culture medium 53 is a gas space 55, which is usually at least 10% of the container volume, and which may be filled with air or water vapor. During the sterilizing operation space 55 will normally mostly contain water in gaseous form. Nipples 57 and 59 are of suitable construction or are provided with sealing members or features so that upon screwing down of fittings 51 pressure-tight seals will be made with tubings 61, 63 and 65. Flexible pressure tubing 63 connects the two pressure retaining containers and tubings 61 and 65 serve to transmit the pressures in their respective containers to separate monitors when the microwave is being controlled manually or to one monitor and one controller. If desired, tubing 63 may be omitted and only a single pressure retaining container may be equipped with fittings and tubes so as to communicate its internal pressure to a controller and to a visual display or monitor. Also, to protect against any undesirably high pressure developing, as an extreme safety measure the container or its fittings may include a pressure relief valve or a rupture disc, not illustrated in the drawing.

Figure 4:
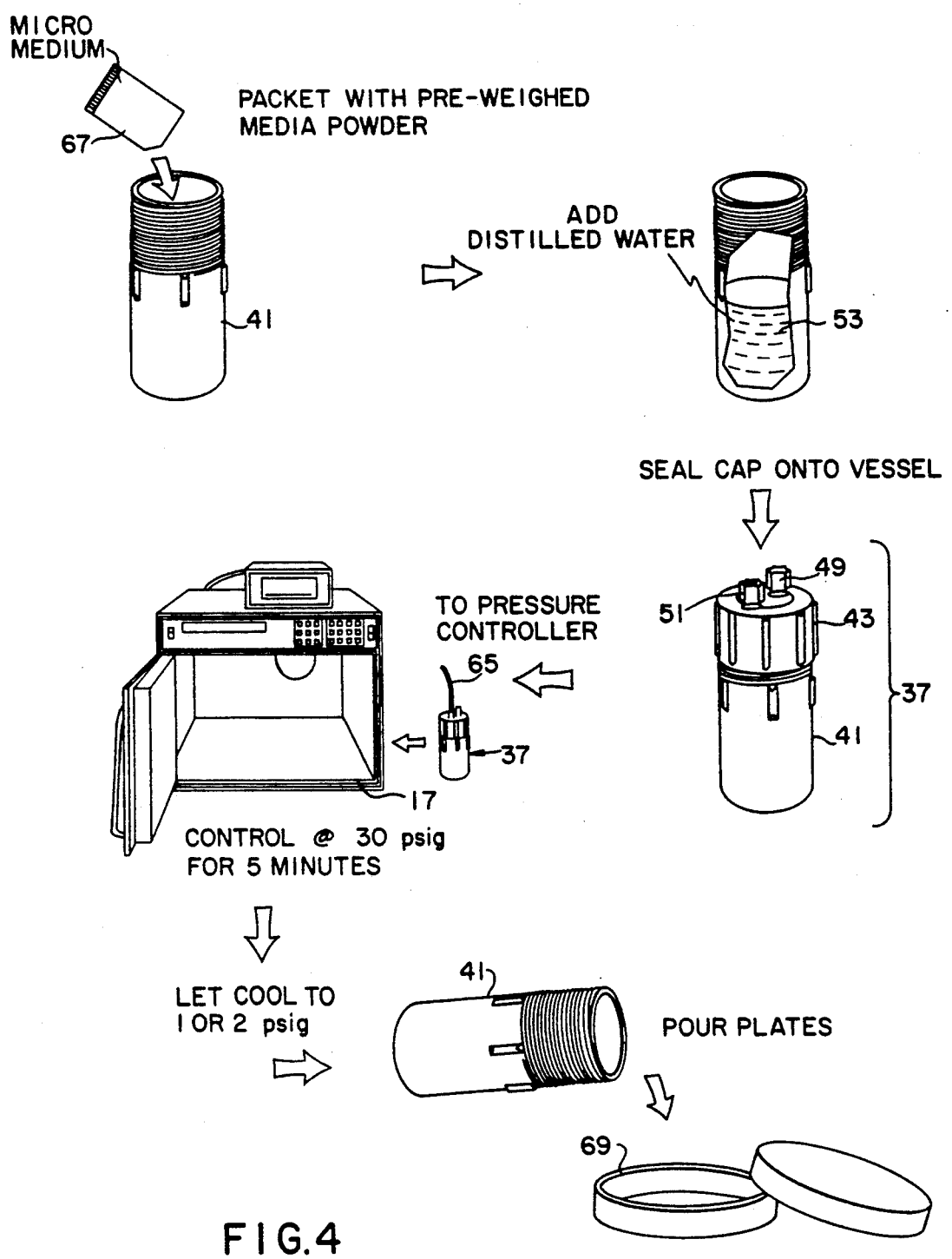
FIG. 4 is a pictorial representation of the invented process and apparatus, with the turntable and containers not being shown.

In FIG. 4 there are pictorially illustrated various steps in the sterilizing procedure, starting with addition of the components or the culture medium to the pressure retaining container and ending with pouring of the sterilized medium into culture plates, such as Petri dishes. As illustrated, a package 67, containing the pre-weighed components of a culture medium (except water) is emptied into cylindrical container 41, after which distilled water, in formula proportion, is added to such container and cap 43 is screwed on, with sealing ring 45 in place, producing the pressure retaining container 37, with a charge of culture medium components ready to be sterilized. Tubing 65 is attached to the container in the manner previously described, the container is inserted into the microwave retaining chamber 17 of the sterilization system apparatus, and tubing 65 is connected to pressure controller 31. As illustrated in FIG. 4, chamber 17 does not contain a turntable and only one pressure retaining container of culture medium is inserted for sterilization. Such represents a minimum sterilizing operation, utilizing only a single container, but a turntable will very preferably be present, to heat the container contents evenly, and a plurality of culture media or a plurality of quantities of the same culture medium will normally be sterilized in the apparatus, with the pressure retaining containers being arranged on the turntable in the manner illustrated in FIG. 1. In such an instance, the container connected to the pressure controller/monitor may be employed only for pressure control and its contents may be water or medium which is not to be incubated (to avoid any even remotely possible contamination). Optionally, two containers, preferably diametrically opposed, may be connected by tubing 63 to equalize or average the pressure therein, and the other ports of the containers may be employed to communicate such pressure with a controller and a monitor. Normally, utilizing charges of culture medium no more than 150 ml. per container and with no more than 20 containers in the apparatus, and employing a suitably powered magnetron, e.g., in the 600 to 2,000 watt range, when the internal pressure generated by heating the culture medium to be sterilized with microwave radiation is raised to 30 psig, five minutes holding at such pressure (and corresponding equilibrium temperature) will sterilize culture media even when such contain massive quantities of microorganisms, even spore-forming microorganisms, such as *Bacillus stearothermophilus*. However, to be absolutely certain that no viable organisms of resistant types survive the sterilization process it may be desirable to utilize a somewhat higher pressure, e.g., 35 or 40 psig, and a somewhat longer sterilization period, e.g., 7 to 9 minutes. Normally, experience will teach the operator of the system at what combination of pressure and sterilizing time complete sterilization is always obtained. After sterilization is complete the container(s) are allowed to cool, usually with the circulating fan of the microwave apparatus running, and when the pressure therein is low, e.g., 1 or 2 psig, the container(s) may be opened by unscrewing cap 43 from cylinder 41, and the sterilized culture medium may be poured out into culture tubes, vessels or plates 69, as indicated. Opening of the container under some slight pressure may sometimes be desirable to maintain the temperature of the medium above its pour point, which is often about 47° C. The sterile medium is then ready for use, except, of course, that media intended to be employed in solid form, such as some agar media, may be allowed to set or gel first.

The biological media being sterilized may include various polar liquid (usually aqueous) culture media, some of which are TSB (trypticase soy broth), TSA (trypticase soy agar), SMA (standard method agar/plate count agar), EMB agar (eosin-methylene blue agar), violet red bile agar, and MSA (mannitol salts agar). Such culture media are only representative of this large class of preparations and virtually any such medium may be sterilized, providing that neither microwave radiation nor the elevated temperature employed significantly adversely affects any component thereof (except microbiological contaminants, if present). Such media may be prepared by the microbiologist or technician or may be pre-mixed and available in packages or pre-weighed packets or envelopes, or in compressed tablet or pellet forms.

The water or other suitable polar solvent or mixture thereof employed as the medium of the culture is preferably distilled water but in suitable circumstances deionized water, and even tap water, may be employed. Artificial sea water may be used when marine organisms are to be grown in the culture medium.

In addition to aqueous biological media, such as bacteriological media, intended for use in growing colonies of microorganisms, the present invention also has applications in sterilizing related biological materials, such as dilution blanks, phosphate-buffered saline solutions, balanced salt solutions and tissue culture media stable components. Other items, e.g., implements employed in measuring, transporting and handling such media, may be sterilized in the described containers by supporting them in the gas phase, above a vaporizable polar solvent, such as water, and directing microwave radiation onto the container to raise the temperature and pressure therein to sterilizing conditions, which are then maintained for a sufficiently long time to ensure sterilization of the implements. Such implements, for example, applicators, wires, stirrers, pipettes, droppers, and mini-syringes, are preferably made of microwave transparent materials but some microwave absorption is tolerable. In a preferred embodiment of this aspect of the invention the implement to be sterilized may be supported above a biological medium that is also being sterilized.

While the invention finds particular use in sterilizing biological media, solutions and implements, the apparatus is also useful for other heating (without necessarily sterilizing) operations as for dissolving, melting, chemically reacting, curing, polymerizing hydrolyzing, etc., wherein controlled elevated temperatures are desirably maintained.

The pressure retaining container is made of a material which is capable of transmitting microwave radiation with little or no absorption thereof, and which is able to retain operating pressures in the container without distortion or leakage at the elevated temperatures and pressures employed. Although various synthetic organic polymeric plastic materials can satisfy these criteria, it is presently highly preferred to employ polytetrafluoroethylene (TEFLON®) for such containers, including the lower cylindrical portions, the caps, the sealing rings and the fittings. It is also preferable to utilize Teflon for the connecting tubing and for the turntable and other parts of the apparatus located in the radiation confining chamber thereof. However, other polymers are also considered useful in these applications, including polyether imide resins, such as UL-TEM®, and polycarbonates, such as LEXAN®.

The microwave sterilization system that is preferred for use in practicing the invented process is preferably the MSS-500 system manufactured by CEM Corporation but other microwave apparatuses may be adapted for such use, including the CEM MSD-81 system, preferably equipped with a microwave transparent turntable which acts as a suitable moving support for a plurality of containers. Similarly, various other microwave apparatuses can be similarly adapted to sterilize biological media and related materials. However, it is desirable for such an apparatus to have a power requirement of at least 600 watts, with a preferable range being from 600 or 1,000 to 2,000 watts. The wattage should be chosen so that the magnetron can quickly heat the biological media and usually, and desirably, such heating to sterilizing pressure and temperature will take less than ten minutes.

The pressure controller is a relatively simple device in which a pressure switch, actuated by the pressure transmitted to it from a container being heated by microwave radiation, cuts out the magnetron when a certain predetermined pressure is reached, and reactivates the magnetron when the pressure drops a certain amount below that predetermined figure. Alternatively, the pressure controller may reduce the level of microwave radiation from the magnetron to that equilibrium amount which just maintains the predetermined desired pressure. In preferred embodiments of the invention such predetermined pressure may be set by the operator of the system. The actual pressure in the "test" container (or the average pressure in a pair or in a plurality of such connected containers) is visually displayed on a screen of the monitor. Any such display device capable of such function may be employed, and such are known in the art. In more complex embodiments of the invention each of the pressure retaining containers may be selectively connected to the visual display so that individual pressure readings may be obtained. However, experience has indicated that such is not necessary because utilizing a turntable or carousel-type support, which oscillates at least 180° and preferably 360°, heating of and pressure development in the individual containers are about the same or are sufficiently close for effective sterilizations.

In the preferred process of the invention the biological medium is poured into the lower cylindrical portion of the microwave transmissive and pressure retaining container or the components of the medium are added to such cylindrical container portion, after which the sealing ring is installed and the cap is tightened in place. At least one fitting of the cap is connected to a pressure controller, which operates the magnetron to keep the pressure at a desired level. One port may be connected to another container and a second port of such other container may be connected to a visual display or monitor. When the containers are not interconnected the other port of the pressure controlling container may be blanked off or may be connected to a monitor. The material of construction of the entire container, including cylinder, sealing ring, cap, nipples and fittings, is preferably of Teflon brand of polytetrafluoroethylene (but other microwave transmissive and heat resistant materials may be substituted in whole or in part).

After placement of the container(s) in the chamber of the microwave sterilization system apparatus the apparatus is turned on and the pressure and temperature of the contents of the containers increase quickly. Such heating process and increasing of pressure to desired level may be speeded by initially utilizing hot water or other hot polar medium for the culture medium components. Because little of the polar medium (water) of the biological medium is vaporized only little heat of vaporization is required. A significant part of the heat-up time is often savable by employing hot water instead of room temperature water.

After the pressure (and related temperature) reaches the desired predetermined level the pressure controller maintains such level, which will be at least 10 psig. Normally such sterilizing pressure will be in the range of 15 to 100 psig, preferably 25 to 50 psig, e.g., 30, 35 or 40 psig. Corresponding temperatures will be at least 113° C. during the sterilizing period, and will be in the range of about 120° to 170° C., preferably about 127° to 145° C., e.g., about 130°, 135° and 138° C.

The sterilizing time, that period during which the temperature of the medium corresponds to the predetermined sterilizing pressure, will normally be up to 10 minutes and preferably will be less than ten minutes. The time employed will be that which is sufficient to sterilize the medium or may be more than such time to make absolutely certain that the medium being treated is sterile. Such time is usually at least 60 seconds and preferably is at least two minutes. Times in the range of 3 to 10 minutes are effective and desirable and in normal operations a preferred time range is from 4 to 7 minutes, e.g., about 5 minutes.

Because speed of sterilization is considered to be important it is desirable to heat the medium to sterilizing pressure and temperature as quickly as feasible and to cool it down as quickly, too, after completion of sterilization. Normally, heat-up times for the containers of media of the types described are in the range of 2 to 10 minutes, using a magnetron of sufficient capacity, and heat-up times may be kept below five minutes, e.g., about 3 or 4 minutes, by employing a 1,500 watt or 2,000 watt unit, and sometimes by using pre-heated water. Similarly, heat-up times are diminished by using smaller charges of media. Thus, it is feasible to reach sterilizing temperature and pressure within 2 to 4 minutes after initiation of the process and often such period may be only 2 to 3 minutes.

After the sterilization period is over it is desirable to cool the containers quickly so that a new batch of media may be processed and so that the overall sterilization time may be kept as short as feasible. Cooling can be effected by continuing the operation of the circulating fan to move air through the system chamber and about the various containers therein. Of course, if the air is colder the cooling will be quicker, so it may be desirable to utilize coolants, such as solidified carbon dioxide (dry ice) or liquid nitrogen or other liquefied gases, e.g., FREONS ® (halogenated lower hydrocarbon), at the inlet port to the chamber. It is also possible to open the apparatus door and direct coolant onto the containers. One may also seal off tubes 61 and 65, the pressure controller and visual monitor tubes, and remove the individual containers, plus tubes, from the apparatus, and immerse them in a cooling fluid, such as room temperature water or ice water. In another version of the invention the turntable or carousel may be removed from the apparatus after sealing off and disconnecting any tubing attached to container fittings, and the entire turntable, with containers held therein, and with the sealed off tubing, may be subjected to cooling. By following such procedures cooling times for lowering the pressure in the various containers to no more than about 3 psig, preferably 1 to 2 psig, can be reduced to from 1 to 10 minutes, preferably being in the range of 1 to 5 minutes and more preferably 1 to 3 minutes. Thus, the total time required to carry out the present process will usually be less than 20 minutes, often being in the range of about 10 to 15 minutes, and may sometimes be even less, such as 8 to 10 minutes.

Additional operator's time is conserved by utilizing powder tableted components of a culture medium and forming the medium by adding water to such components in the container to be subjected to microwave radiation, thus actually making the culture medium in the container as the components are dissolved and distributed throughout the liquid medium during the microwave heating thereof. This saves a separate dissolving operation and avoids the deposition of culture medium on the upper portion of the container wall, where it could interfere with sealing, and might not be sterilized if it dried and was then shielded by the sealing ring from the liquid medium and the steam in the container.

Although the described heating and sterilization are operative when a single container or a plurality of containers of culture medium or other material is/are held stationary during the microwave sterilization operation, to make sure that the microwave radiation is evenly applied to such material, especially when a plurality of containers of such is present, it is considered to be highly advantageous for the various containers and the material(s) in them to be kept in motion during the sterilization process. A continuously rotating turntable may be employed but such requires a complicated connection of the pressure controller and monitor to the container(s). By utilizing oscillatory (and rotational) motion and flexible tubings such connections are not required. Different degrees of oscillation are useful and all will improve the equalization of microwave radiation onto the different culture media being sterilized. However, it is preferred for the oscillation to be in the range of 180° to 360°, and a 360° oscillation is most preferable for most even application of such sterilizing radiation to the containers and to their contents, but rotations of as little as 90° are useful and those up to 540° are operative. Even application of microwave radiation is important in the present invention because, especially when only a single container is monitored and is employed as the basis for pressure control (or when an average of the pressures in two containers is similarly employed, it is important that the other containers in the system should have essentially the same amount of microwave radiation applied to them, so that the culture media therein will be similarly raised to sterilizing pressure (and temperature). In experiments that have been run it has been found that the same complete sterilizations were obtained in all containers tested, providing that the described sterilizing conditions were employed, evidencing that sufficiently effective radiation onto them was achieved and useful and effective sterilizing pressures and temperatures were obtained. The frequency of oscillations does not appear to be of great importance but normally such will be from 3 to 20 per minute, preferably 4 to 10, e.g., 5 or 6.

Although one may sterilize a larger number of containers of biological media, with sterilizations of as many as 50 or 100 being possible, it will usually be preferred to so treat no more than twenty containers at a time, with ranges of numbers of containers being from 1 or 2 to 20, preferably 5 to 15 and more preferably 10 to 14, e.g., about 12. Such a number of containers of media will conveniently fit in normally sized microprocessor driven microwave units and can be rapidly heated by such units of reasonable power, from 600 to 2,000 watts. The media to be sterilized will normally be of a volume of 10 to 200 ml. per container, preferably 20 to 150 ml., more preferably 50 to 120 ml., e.g., 60 ml. and 100 ml. The containers employed will usually be of sizes in the range of 20 to 400 ml., preferably 75 to 150 ml., e.g., 100 and 125 ml. Using a plurality of such smaller containers, rather than a single larger container, provides greater pressure resistance per container wall thickness, and facilitates cooling and "handling" of the sterilized media.

The invented process provides a quick way to sterilize biological media, such as culture media for bacteria. It can be difficult to measure temperatures in microwave systems like that of this invention (the probe itself might contribute to an erroneous indication of the temperature of the test container), and therefore applicants' discovery that the measurement of pressure developed in a representative container is a simple and feasible way of controlling the sterilization operations, is significant. Utilization of the turntable or carousel, which promotes even heating of the various media, allows the pressure reading for a control container to be sufficiently representative to ensure that the media will be satisfactorily sterilized when one employs sterilization pressures and times that have been established to be satisfactory. The oscillating movements of the various containers of media allow simple tubing connections to the pressure controller and to pressure monitors, and obviate more complex connections.

The preferred microwave sterilization system of this invention rapidly sterilizes bacteriological media and dilution blanks that are employed in total plate count procedures. Total plate counts or total viable counts (TVC) are made to determine the number of bacteria present in a particular sample or specimen. TVC's are routinely performed in quality control laboratories in meat and dairy plants and in waste water treatment plants, for examples. In such laboratories the pour plate method is typically employed, in which the sample is transferred to a sterile, empty Petri dish. A sterile and melted bacteriological agar medium, usually referred to as standard method agar (SMA), is then poured into such dishes, the plates are swirled gently for proper mixing and good distribution of bacteria throughout the medium, and the medium is then allowed to solidify, after which the plates are incubated. Following incubation, which can take from 24 to 48 hours, the number of colonies that have grown in the medium is counted and, based on the dilution factor, the number of bacteria present in the original sample is determined. The present microwave sterilization system is intended for employment in laboratories which perform total plate counts on a regular basis. In addition to SMA, other media, which may be referred to as selective and differential media, are also employed by such laboratories on a regular basis, usually in smaller amounts and sometimes on short notice. The present invention permits quick sterilizations of a plurality of quantities of one medium or of a variety of media. Using the apparatus illustrated in FIG. 1, as much as 1.2 l. of medium or media may be heated, sterilized and cooled to the point where such can be used, in about 10 to 15 minutes, or as little as 25 ml. can be made at one time. Because a number of relatively small containers is employed a variety of media can be sterilized at one time, and the operations proceed quickly.

The present system is also intended for use in hospital microbiology laboratories wherein various selective/differential media are employed and usually are needed in varying amounts and at varying times and frequencies. Currently in such laboratories, laboratory personnel must take significant times from their normal duties to prepare and sterilize the media, or the laboratories must purchase previously prepared and sterilized media, which are unduly expensive. The present invention saves both working time and money for such laboratories.

As was previously mentioned, other polar materials and implements may also be sterilized, using the present systems, and therefore laboratory personnel and other users of the process will find other uses for the system, and it is not limited to the sterilization of culture media.

The invented process is much more efficient and convenient than autoclave sterilization. The autoclaves that are connected to a source of steam are not readily portable and have to be kept "on line". When the autoclave is electrically heated it may be portable but the resistance heating to desired pressure of the autoclave and the heatings of the containers thereof are considerably slower than the heating to sterilizing conditions of biological media in the invented microwave sterilization system. In such autoclave water must first be converted to steam and the steam then has to heat the container of media whereas microwaves heat the medium directly, saving energy. The Teflon containers are transparent to microwaves and therefore do not impede the direct heating of the medium, and the container is not heated by the microwave radiation. In addition to the longer time it takes to heat the electrical autoclave to sterilizing pressure, it also takes longer to cool it down. In both the steam and electrical autoclaves the entire autoclave is under pressure and the entire autoclave must be cooled down before the seal thereof can be safely broken to remove sterilized items. An important advantage of the present invention is that the microwave sterilizing system chamber is not under pressure and the door can be opened at any time after sterilization, with individual containers being coolable quickly to a safe pressure, at which they may be opened and the sterilized culture medium may be poured out. The Teflon containers are strong enough to resist any designed pressures that are employed and they can operate at pressures higher than those feasible for a comparably sized autoclave of similar capacity. The microwave sterilizing system (MSS) apparatus is readily portable, which makes for convenient transportation thereof and use in a wide variety of locations in which the use of autoclaves would be inconvenient, dangerous or impossible. Thus, marine biology laboratories aboard small ships or boats can conveniently employ the present processes, as can mobile laboratories. The invented systems and processes are lighter and safer, and useful laboratories aboard spacecraft and on space stations, and because the sterilization is under pressure they are superior to "atmospheric" sterilizations (as by boiling) in areas of low pressure, such as at high altitudes on earth, and in aircraft and space vehicles.

Although the advantages recited make a clear case for superiority of the invented process over autoclaving, another very significant advantage to the user of the process is its simplicity. The system may be digitally controlled so that it requires virtually no attention by the operator. All he or she has to do is add the components to the containers, connect one or more of the containers to the pressure controller and monitor, position them in the turntable and press the ON button. Heat-up can be conducted automatically and the media will be held at sterilizing pressure for the required time, after which the containers will be cooled. The apparatus may even be programmed to emit a signal to the operator when the pressures in the containers are low enough to allow for safe opening, and utilization of the contents. Such pressures will usually be those in the range corresponding to temperatures in the range of 46° to 50° C. for agar plate media, because below 46° C. such media tend to become difficult to pour.

The following examples illustrate but do not limit the invention. Unless otherwise indicated, in these examples and the specification and the appended claims all parts are by weight and all temperatures are in °C.

EXAMPLE 1

1.41 Grams of SMA powder mix, obtained from Difco Laboratories, Detroit, Mich., are placed in each of twelve substantially cylindrical TEFLON containers like those illustrated in FIGS. 1–4, of approximately 125 ml. capacities, and 60 ml. of distilled water are added to each of the containers, after which the powders and the waters are mixed. The SMA powder mentioned includes five parts of Bacto tryptone, 2.5 parts of Bacto yeast extract, one part of Bacto dextrose and 15 parts of agar agar. The powder and water are then stirred or otherwise mixed to make suitable mixtures, and the cylinders are capped, with two of them being connected together and communicated with a pressure controller, and a pressure monitor (visual display) by means of TEFLON flexible tubings, as indicated in the figures. The two connected containers are located about 180° apart, which is considered most desirable for obtaining the most representative average pressures for all the containers. The microwave system employed, a modified CEM MDS-81, operates at 2.45 gigahertz, with a power output of 1,500 watts. However, under suitable circumstances power ranges of 600 to 2,000 watts (or more) are operative and the microwave radiation may be in the range of 0.3 to 50 gigahartz (or more), preferably being in the range of 0.8 to 3 gigahartz. The ON button is then pressed and microwave energy is directed into the system chamber. At the same time, the turntable is oscillated in a horizontal plane, at six 360° oscillations per minute. The digital controls are set for a sterilizing operation at 30 psig and that pressure is reached in about four or five minutes, after which the microwave radiation is controlled by the pressure controller so as to maintain such pressure by switching the magnetron on and off, over the next five minutes, after which the magnetron is automatically turned off and the containers of media are allowed to cool, with the system fan or blower operating. Such cooling takes three or four minutes, during which time the pressures in the containers drop to about 1 psig. The containers are then opened and the contents thereof are then poured into sterile Petri dishes and are incubated at 37° C. for 48 hours, after which they are examined for growths of any bacterial colonies. No such growths are observable, which indicates that all the media prepared have been successfully sterilized. Thus, 0.7 l. of sterile medium are prepared, enough for 50 to 60 plates, in a total time of about thirteen minutes, by the procedure of this invention. To sterilize such quantity of medium in a resistance heated autoclave often takes about an hour, so the saving in time is evident.

When 1.80 g. of Trypticase soy broth, 2.70 g. of Trypticase soy agar, 2.16 g. of EMB agar, or 2.49 g. of violet red bile agar are employed, each with 60 ml. of distilled water, using the same procedure as previously described in this example, sterile media result. Despite the different contents of polar solutes in the different media, when such different media are filled into different containers for sterilization, so that during the sterilization operation two containers each of such five different media are being sterilized at the same time, heatings of all the media are sufficiently equal so that all are sterilized under the described conditions.

The same results are obtainable using a sterilization period of three minutes at 30 psig but for safety's sake it will usually be desirable to conduct the sterilization over a five minute period and sometimes at even more elevated pressures, such as 35 or 40 psig.

EXAMPLE 2

Although the experiments of Example 1 clearly show that the processes of this invention are exceptionally useful for rapidly sterilizing biological media, such as media for bacterial cultures, more severe tests of the sterilization process were run, with extremely high concentrations of bacteria being added to the medium before sterilization. Such tests are clearly unrealistically severe but were run to verify the capabilities of the process, even under such artificial adverse conditions.

The same process described in Example 1 was run but contaminating bacteria were added to two containers for each of the spiking contaminants. The bacteria added were *Bacillus subtilis* (ATCC 6633), *Escherichia coli* (ATCC 11229) and *Pseudomonas aeruginosa* (ATCC 15442). The inocula employed contained 48,000, 360,000, and 55,000 cells, respectively.

After the sterilization procedure the previously inoculated media were poured into sterile Petri dishes and were incubated for 48 hours at 37° C., after which the plates were examined for any evidence of growths of bacterial colonies. No such growths were observed.

In a modification of the above experiments a perforated Teflon shelf is positioned in each of the containers of spiked media, so that the shelf tops are about 3 cm. above the surfaces of the media, and after charging of the media to the cylinders LEXAN implements, previously contaminated with the same bacteria, are placed on the shelves. Subsequently, the sterilized media, in the sterile Petri dishes, are contacted by the implement that was also sterilized so as to transfer to the media any viable bacteria still on the implement. After incubation of the various media no bacterial growth is observed.

In a further modification of this experiment (without implements) the contaminating bacteria are mixed and two containers of each medium are inoculated with such mixture. After sterilization by the described process and incubation of the media in sterile Petri dishes for the prescribed time and at the prescribed temperature, no bacterial growth is observable.

EXAMPLE 3

In another severe test of the invented process the spore-forming bacterium *Bacillus stearothermophilus* was employed to spike the media to be sterilized. The procedure followed was that of Example 2, using SMA as the medium and employing 400,000 cells. Incubation was conducted at 55° C. instead of 37° C. and after 48 hours four colonies were observed. Thus, although the sterilization procedure had decreased 400,000 cells to 4 viable cells it had not been completely successful. However, when the pressure in the container is increased to 40 psig, and even when it is increased to 35 psig, completely sterile media are obtainable. Similarly, when *Bacillus stearothermophilus* is mixed with the other mentioned bacteria and such mixture is employed to spike the culture medium, the medium is completely sterilized when the sterilizing pressure is maintained at 35 psig or 40 psig or higher, for five minutes. Such is also the case when the other media mentioned in Example 2 are substituted for SMA.

EXAMPLE 4

In other modifications of the invention the apparatus and materials utilized to make the microwave sterilization system may be modified. For example, the containers and turntable may be made of Lexan and the pressure transmitting tubing may be made of polypropylene. Instead of employing a fan to cool down the containers such cooling may be effected by opening the system apparatus door and directing either gaseous or liquid coolant onto the containers, while they are still in the chamber or after removal thereof, with the turntable. Different powered magnetrons may be utilized and of course, the microwave radiation may be of different frequencies in ranges given, as it is in various countries other than the United States.

In normal laboratory operations the microbiologist or laboratory technician will run a series of experiments with the media materials normally employed in such laboratory to determine the optimum conditions for sterilization. Thus, it is expected that many such laboratories will find that sterilization times, including heat-up and cool-down times, much shorter than those given in these examples, will be satisfactory to ensure the sterilizations of all media that they are using.

In other experiments dilution media, phosphate-buffered saline solutions, balanced salt solutions and tissue culture media (except for heat sensitive components thereof) are satisfactorily heated, under pressure, and sterilized in the described containers, following the procedures of these examples.

As is seen from the foregoing examples and the other parts of this specification, there has been provided a procedure which is simple to practice, economical, safe, convenient and effective. Compared to the standard method of sterilizing culture media, autoclaving, it represents a significant step forward, and consequently it is expected that it will be recognized as being easier and faster than autoclaving and as accurate. Although sterilization of biological media is a preferred embodiment of the process aspect of this invention, such processes also include heatings without sterilizations, such as heatings to dissolve soluble compounds in water, to melt materials, such as biological media, to chemically react reactants, and to cure, polymerize or hydrolyze materials, in modifications of the processes of the foregoing working examples.

The invented process provides a faster heating and sterilization procedure than autoclaving, is convenient, safe, economical and easy to practice, and the results are excellent. It is expected that such processes and the equipment utilized in them will substantially replace conventional autoclaving operations and apparatuses in many bacteriological laboratories in the future.

This invention has been described with respect to specific illustrations and examples thereof but is not to be limited to these because it is evident that one of skill in the art will be able to utilize substitutes and equivalents without departing from the invention.

What is claimed is:

1. A process for heating aqueous material in a container under pressure to a desired elevated temperature level or range and maintaining it at that level or range which comprises applying microwave radiation to such material in a closed pressure retaining container by directing microwave radiation through the container and onto the material in the container while the container is moving in oscillating rotational motion so that the pressure and temperature in the container are elevated, with the container interior being connected by connecting means to a controller, which is activated by the pressure in the container, which controller controls the microwave radiation onto the container and its contents so that the pressure in the container is maintained at such a level or in such a range as to cause the temperature therein to be at the desired level or in the desired range.

2. A process according to claim 1 wherein the material in the container is aqueous, the pressure in the container is controlled to be at least 10 pounds per square inch gauge (psig) and the temperature in the container is thereby controlled to be at least 113° C.

3. A process according to claim 2 wherein the pressure in the container is controlled to be in the range of 15 to 100 psig.

4. A process for sterilizing biological media which comprises applying microwave radiation to an aqueous biological medium, contained in a microwave transmissive pressure retaining container, by directing microwave radiation through the container and onto the medium in such amount that the pressure in the container and the temperature of the medium are raised above ambient pressure and temperature, and maintaining such raised pressure and temperature for a time sufficient to sterilize the medium by controlling the pressure in the container with a controller which is operatively connected to the container and which controls the application of microwave radiation to the container and contained aqueous biological medium by controlling operation of a source of microwave radiation in response to pressure in the container.

5. A process according to claim 4 wherein components of the biological medium, in powder or tablet form, and water are added to the container prior to applying the microwave radiation, and the biological medium is formed as such components are dissolved in the water during the sterilizing heating thereof by the microwave radiation.

6. A process according to claim 4 wherein the aqueous biological medium is suitable for growing bacterial colonies, the microwave transmissive, pressure retaining container is located in a microwave radiation confining chamber of a microwave apparatus, the sterilizing time is between 60 seconds and 10 minutes, the pressure during such sterilizing time is at least 10 psig and the temperature is at least 113° C. during such sterilizing time.

7. A process according to claim 6 wherein the aqueous biological medium is a broth or gel forming medium, the pressure during sterilizing is in the range of 15 to 100 psig and the temperature is in the range of 120° to 170° C.

8. A process according to claim 7 wherein the aqueous biological medium is a soy broth or an agar plate medium, the container is formed of polytetrafluoroethylene, the sterilizing time is about 5 minutes, the pressure during such sterilizing time is 30 to 50 psig, and the temperature during such sterilizing time is about 130° C.

9. A process according to claim 6 wherein the sterilizing pressure is controllably maintained in the range of 15 to 100 psig during the sterilizing time and the container is kept in motion during such time to promote even heating of the medium therein.

10. A process according to claim 9 wherein said medium is contained in a plurality of microwave transmissive, pressure retaining container in said chamber of a microwave apparatus, at least two such containers are interconnected at or near tops thereof and are communicated with said pressure controller, and such plurality of containers is kept in motion by a turntable in the microwave apparatus chamber.

11. A process according to claim 10 wherein the number of containers is in the range of 2 to 20, each of which has an operating capacity in the range of 10 to 200 ml. of biological medium, the microwave apparatus is digitally controllable, and the turntable oscillates 180° to 540°.

12. A process according to claim 11 wherein the number of containers is about 12, each has an operating capacity of about 100 ml. of biological medium, the turntable rotationally oscillates about 360° about six times per minute and the pressure in at least one of the containers is indicated on a monitor.

13. An apparatus for heating material in a pressure retaining container which comprises a microwave chamber, a source of microwave radiation, a turntable in the microwave chamber that is capable of movement in oscillating rotational motion, a pressure responsive controller which controls the source of microwave radiation in response to pressure communicated to it, and means for connecting the controller with the pressure retaining container for the material to be heated when such container is on the turntable, which is in oscillating rotational motion.

14. An apparatus according to claim 13 for sterilizing the material being heated, wherein the turntable is horizontal and is capable of supporting 1 to 20 containers of material to be sterilized, and is movable at 3 to 20 oscillations per minute, with the oscillations being in the 180° to 540° range.

15. An apparatus according to claim 14 wherein at least two containers are on the turntable and said at least two containers have interiors thereof connected together by tubing so that the pressure transmitted to the controller during sterilization of the material being heated is an average pressure of the connected containers, which is in the range of 10 to 100 psig.

16. An apparatus according to claim 15 wherein the connecting means is flexible polytetrafluoroethylene tubing.

17. An apparatus according to claim 16 wherein the oscillations of the turntable are about 360° and they occur about six times per minute, and the pressure during said sterilization is in the range of 30 to 50 psig.

* * * * *